(12) United States Patent
Inui

(10) Patent No.: US 8,080,372 B2
(45) Date of Patent: Dec. 20, 2011

(54) METHOD FOR DETECTING NUCLEIC ACID IN SAMPLE, METHOD FOR DESIGNING PROBES, SYSTEM FOR DESIGNING PROBES THEREFOR

(75) Inventor: Mimune Inui, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/098,994

(22) Filed: Apr. 7, 2008

(65) Prior Publication Data

US 2008/0254472 A1    Oct. 16, 2008

(30) Foreign Application Priority Data

Apr. 11, 2007  (JP) .................................. 2007-103853

(51) Int. Cl.
  *C12Q 1/68* (2006.01)
  *C07H 21/02* (2006.01)
  *C07H 21/04* (2006.01)
(52) U.S. Cl. ........................... 435/6; 536/23.1; 536/24.3
(58) Field of Classification Search ...... 435/6; 536/23.1, 536/24.3
  See application file for complete search history.

(56) References Cited

U.S. PATENT DOCUMENTS

| | | | | |
|---|---|---|---|---|
| 5,605,662 A | * | 2/1997 | Heller et al. ................ | 422/68.1 |
| 5,747,244 A | * | 5/1998 | Sheridan et al. ............ | 435/6 |
| 5,750,338 A | * | 5/1998 | Collins et al. ............... | 435/6 |
| 5,804,384 A | * | 9/1998 | Muller et al. ............... | 435/6 |
| 6,013,440 A | * | 1/2000 | Lipshutz et al. ............ | 506/7 |
| 7,320,862 B2 | * | 1/2008 | Stahler et al. .............. | 435/6 |
| 2004/0241643 A1 | | 12/2004 | Yamamoto et al. | |
| 2005/0009020 A1 | * | 1/2005 | Distler ........................ | 435/6 |
| 2005/0059069 A1 | | 3/2005 | Suzuki et al. | |
| 2006/0134615 A1 | * | 6/2006 | Linder et al. ............... | 435/5 |
| 2006/0269933 A1 | | 11/2006 | Inui | |
| 2007/0248957 A1 | * | 10/2007 | Nova et al. ................. | 435/6 |
| 2008/0076130 A1 | * | 3/2008 | Guo ............................ | 435/6 |
| 2008/0081328 A1 | * | 4/2008 | Linnen et al. .............. | 435/5 |
| 2008/0125324 A1 | * | 5/2008 | Petersdorf et al. ......... | 506/1 |
| 2008/0146791 A1 | * | 6/2008 | Stahler et al. .............. | 536/25.41 |
| 2008/0176242 A1 | * | 7/2008 | McMaster et al. ......... | 435/6 |
| 2008/0194413 A1 | * | 8/2008 | Albert ......................... | 506/1 |

FOREIGN PATENT DOCUMENTS

JP       2004-313181 A    11/2004

OTHER PUBLICATIONS

Miyachi et al., Application of polymer-embedded proteins to fabrication of DNA array. Biotechnology and Bioengineering 69 (3) : 323-329 (2000).*
Okano et al., Position-specific release of DNA from a chip by using photothermal denaturation. Sensors and Actuators B 64 : 88-94 (2000).*
Ranki et al. Sandwich hybridization as a convenient method for the detection of nucleic acids in crude samples. Gene 21 : 77-85 (1983).*
Jeffreys et al., DNA enrichment by allele-specific hybridization (DEASH): a novel method for haplotyping and for detecting low-frequency base substitutional variants and recombinant DNA molecules. Genome Research 13 (10) : 2316-2324 (Oct. 2003).*

* cited by examiner

*Primary Examiner* — Ethan C Whisenant
(74) *Attorney, Agent, or Firm* — Fitzpatrick, Cella, Harper & Scinto

(57) ABSTRACT

Accurate detection of a target microorganism from a sample, which may contain a plurality of microorganisms, is intended. This can be realized by eliminating a possibility of cross-hybridization of a microorganism with other probes, which can accelerate the designing speed, detecting microorganisms one-by-one in the designed order, and absorbing all the existing microorganisms.

9 Claims, 8 Drawing Sheets

METHOD FOR DETECTING NUCLEIC ACID IN SAMPLE, METHOD FOR DESIGNING PROBES, SYSTEM FOR DESIGNING PROBES THEREFOR

BACKGROUND OF THE INVENTION

1. Field of the Invention

The present invention relates to a method for detecting a nucleic acid contained in a target organism in a sample, a probe design method, and a probe design system therefore. More particularly, the present invention relates to a method for detecting DNA, which may originate from microorganisms etc. and exist in a sample, such as blood, based on a novel designing technology of probes.

2. Description of the Related Art

It is desired to treat a patient suspected of combined infection more quickly and appropriately.

To that end it is necessary to identify accurately microorganisms infecting the subject patient. A method for identifying microorganisms in a sample by hybridizing a DNA extracted from the sample, such as blood taken from a patient, with a probe specific to a possibly infected microorganism, and detecting a hybrid product, is under study as one of the methods. The accuracy of the detection of microorganisms in a sample depends on the designed specificities of probes for the respective microorganisms to the DNA corresponding to such respective microorganisms. For example using a probe hybridizing to both *Staphylococcus aureus* and *Pseudomonas aeruginosa*, it is not possible to identify accurately microorganisms. In other words, it is important to design a probe capable of avoiding cross-hybridization for an accurate identification of microorganisms. The present inventors have applied a patent disclosing a probe including nucleotide sequences discriminating separately a plurality of infectious pathogenic microorganisms (Japanese Patent Application Laid-Open No. 2004-313181). However, if in the future, a need occurs to detect more diversified microorganisms in a sample, a plain extension of the technology requires discovering a unique sequence specific to each of all such diversified microorganisms. This requires increased number of calculations demanding a long time for designing probes.

Further, with increase of the numbers of the target microorganisms, it is expected that such unique nucleotide sequence cannot be selected any more with respect to a certain microorganism, as is completely free from any cross-hybridization with all target microorganisms other than said microorganism.

SUMMARY OF THE INVENTION

The present invention provides a method to detect accurately and simply a target DNA in a sample, which may potentially contain various DNAs from microorganisms, etc.

The present invention further provides a method to detect a target DNA in a sample, which may potentially contain various DNAs from microorganisms, etc., with a higher degree of freedom in probe design.

A method according to the present invention for detecting a nucleotide acid in a sample, includes; a first step, in which a singularity or a plurality of first probes capable of specifically capturing a particular nucleotide sequence out of a plurality of nucleic acid sequences potentially present in the sample are prepared and the first probes capture the nucleotide sequence in the sample, a second step, in which a plurality or a singularity of second probes capable of specifically capturing a particular nucleotide sequence out of the plurality of nucleic acid sequences excluding the nucleic acid captured by the first probes are prepared and the second probes capture the nucleotide sequence in the sample having passed through the first step, and detecting the presence or amount of at least one of nucleic acid sequences captured in the first step and the second step.

The present invention further provides a probe design method to execute appropriately the aforementioned method.

More particularly, the probe design method according to the present invention is a probe design method for designing one-by-one a partial sequence specific to a particular nucleotide sequence out of a plurality of target nucleotide sequences, and including; selecting a first sequence out of the plurality of target nucleotide sequences, determining out of partial sequences of the first sequence a first partial sequence, which is not identical to any part of the partial sequences of the target nucleotide sequences excluding the first sequence, thereby determining the first partial sequence for a first probe, excluding the first nucleotide sequence from the target sequences and selecting a second sequence out of the target sequences, and determining out of partial sequences of the second sequence a second nucleotide sequence, which is not identical to any part of the partial sequences of the target nucleotide sequences excluding the second sequence, thereby determining the second partial sequence for a second probe.

According to the present invention, even with a large number of DNA kinds, a nucleotide sequence specific to each other can be efficiently discovered for designing probes. Further, the same can relax restrictions on probe designing, and enables probe designing with higher degree of freedom in selecting nucleotide sequences specific to the respective DNAs.

Further features of the present invention will become apparent from the following description of exemplary embodiments with reference to the attached drawings.

DESCRIPTION OF THE EMBODIMENTS

Figure 1:
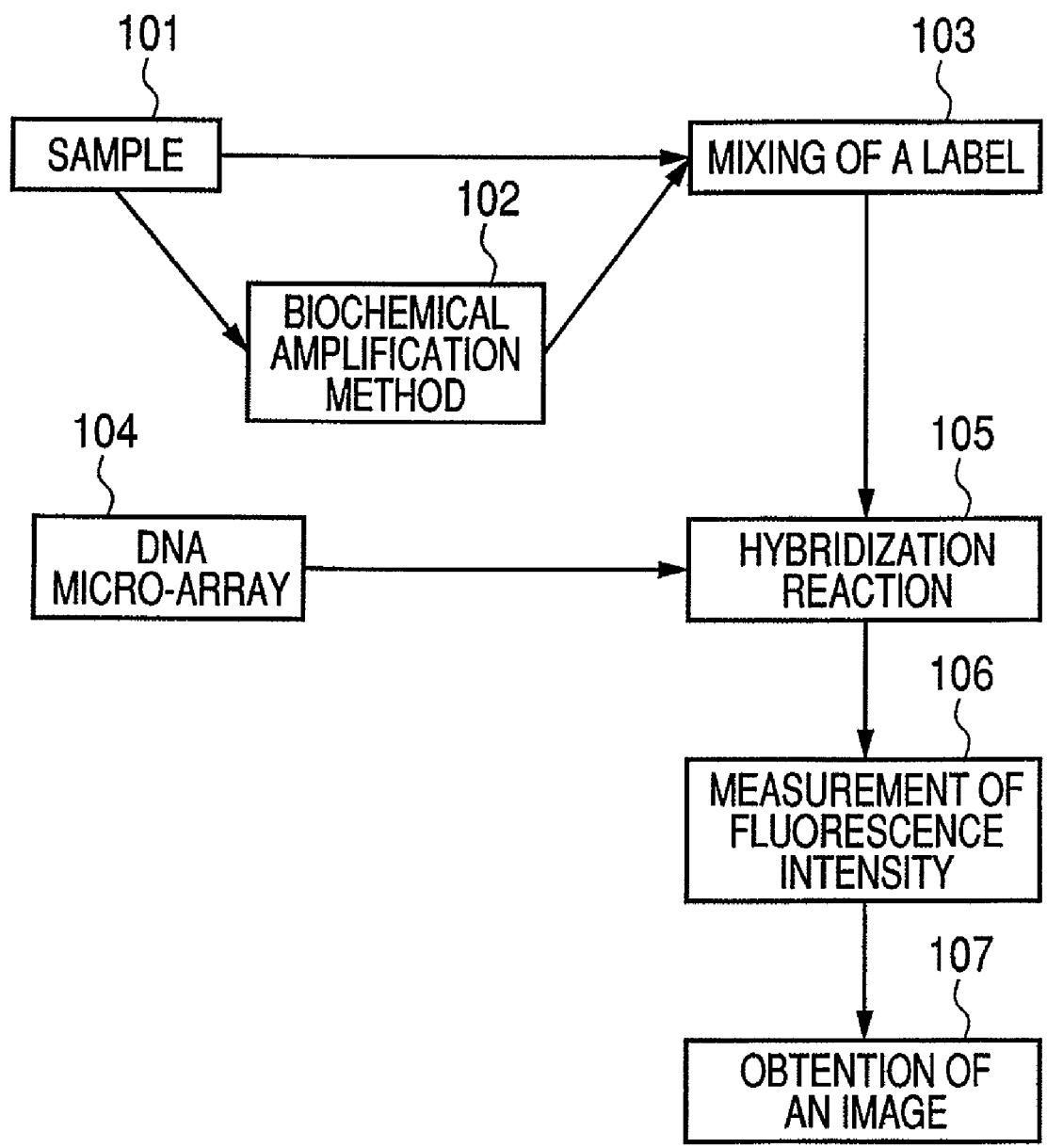
FIG. 1 is a diagram illustrating a detection method according to the present invention.

The present invention will be described in more detail hereinbelow.

A method according to the present invention for detecting a nucleic acid in a sample, includes a first step, in which a singularity or a plurality of first probes capable of specifically capturing a particular nucleotide sequence out of a plurality of nucleic acid sequences potentially present in the sample are prepared and the first probes capture the nucleotide sequence in the sample; a second step, in which a plurality or a singularity of second probes capable of specifically capturing a particular nucleotide sequence out of the plurality of nucleic acid sequences excluding the nucleic acid captured by the first probes are prepared and the second probes capture the nucleotide sequence in the sample having passed through the first step, and detecting the presence or amount of at least one of nucleic acid sequences to be captured in the first step and the second step.

In the above embodiment, the aforementioned steps are minimum requirement, and, after the second step, a step 3 for capturing with third probes capable of specifically capturing a particular nucleotide sequence out of the plurality of nucleic acid sequences excluding the nucleic acid sequences captured by the first and second probes may be added. Preferably step 4, step 5 . . . . step n (n is an integer) should be repeated similarly to capture all the N-kinds of target sequences to be detected.

The present invention is characterized in that target sequences captured in preceding steps are excluded in a next step from specificity comparison objects, thus relaxing specificity criteria imposed by the target sequences and thereby increasing the specificities of the partial sequences of the respective sequences.

The nucleotide sequence captured by the first probe in the first step is practically excluded from the sample, but, by capturing a nucleic acid in a sample by hybridization reaction, it is impossible to capture completely the nucleic acid. Therefore "practically" capturing in this step means that so much of the nucleic acid is captured without influencing the capture in the next step by the second probe. Since the existence of the influence can be judged by detecting the nucleic acid sequences captured in the next step, it is preferable to examine the influence previously by a preparatory experiment in the existence of a nucleic acid to be captured by the first probe.

A step for detection according to the present invention may be after the first step and before the second step, after completion of both the steps 1 and 2, or simultaneously with either of the steps.

The procedures of the first step and the second step may be carried out on a same or different reaction areas.

"A sample" herein refers to an object specimen for inspection or detection, which may contain a singularity or a plurality of target nucleic acids.

The sample may be in a form of liquid, solid or gel. For instance, for identifying pathogenic microorganisms, a sample can be such various substances, in which microorganisms may exist, as body fluids, such as blood, expectoration, gastric juice, vaginal excreta, intraoral mucus, and excrement, such as urine or feces, originated from humans or animals, such as domestic animals. Further, a sample can be a medium, which may be contaminated by microorganisms, such as food causing food poisoning or contamination, water in environment as drinking water or hot spring water, and filters of an air cleaner or a water purifier. Further, an animal or a plant at import and export quarantine can be an object as a sample.

There are many test methods targeting DNA as a test object, including detection of infectious pathogenic microorganisms, cancer diagnosis and detection of genetic polymorphism.

For the purpose of diagnosing an infectious disease, a sample will be a specimen containing a DNA of infectious pathogenic microorganisms existing in blood or an affected part.

For the purpose of detecting a unique gene expressing in a cancer cell, a sample will be a specimen containing the gene and the amplified products thereof.

For the purpose of detecting a human genetic polymorphism, a sample will be a specimen containing nucleic acids having the target genetic polymorphism.

The samples are preferably pretreated suitably for hybridization by a probe, namely a capturing treatment. For example the sample should be preferably subjected to a removal treatment of a substance influencing the hybridization reaction, or a specific amplification treatment of a DNA other than the target DNA.

Next, an embodiment of a detection method will be described using FIG. 1.

The flow of the test illustrated in FIG. 1 will be described based on concrete test procedures envisioning the identification of infectious pathogenic microorganisms. The biological identification method according to the present invention is not limited to the identification of infectious pathogenic microorganisms as described below, but also applicable to determination of human constitution, such as MHC, or analysis of DNA and RNA related to a disease, such as cancer.

A sample 101 as described above should be prepared.

Next, the sample 101 is amplified by a biochemical amplification method 102. For example, for the identification of infectious pathogenic microorganisms, a target nucleic acid is amplified by the PCR method using primers for PCR reaction designed for detection of 16s rRNA, or PCR amplified products are subjected to a preparation by a further PCR reaction. An amplification method other than PCR, e.g. an LAMP method may be applied to preparation.

Then the nucleic acids amplified by a biochemical amplification method 102, or the nucleic acids contained in the sample 101 per se are labeled for visualization by any of various labeling methods (mixing of a label 103). As labeling substance, a fluorescent substance is in general used, such as Cy3, Cy5 and rhodamine. A labeling molecule may be added at the biochemical amplification 102.

Figure 3:
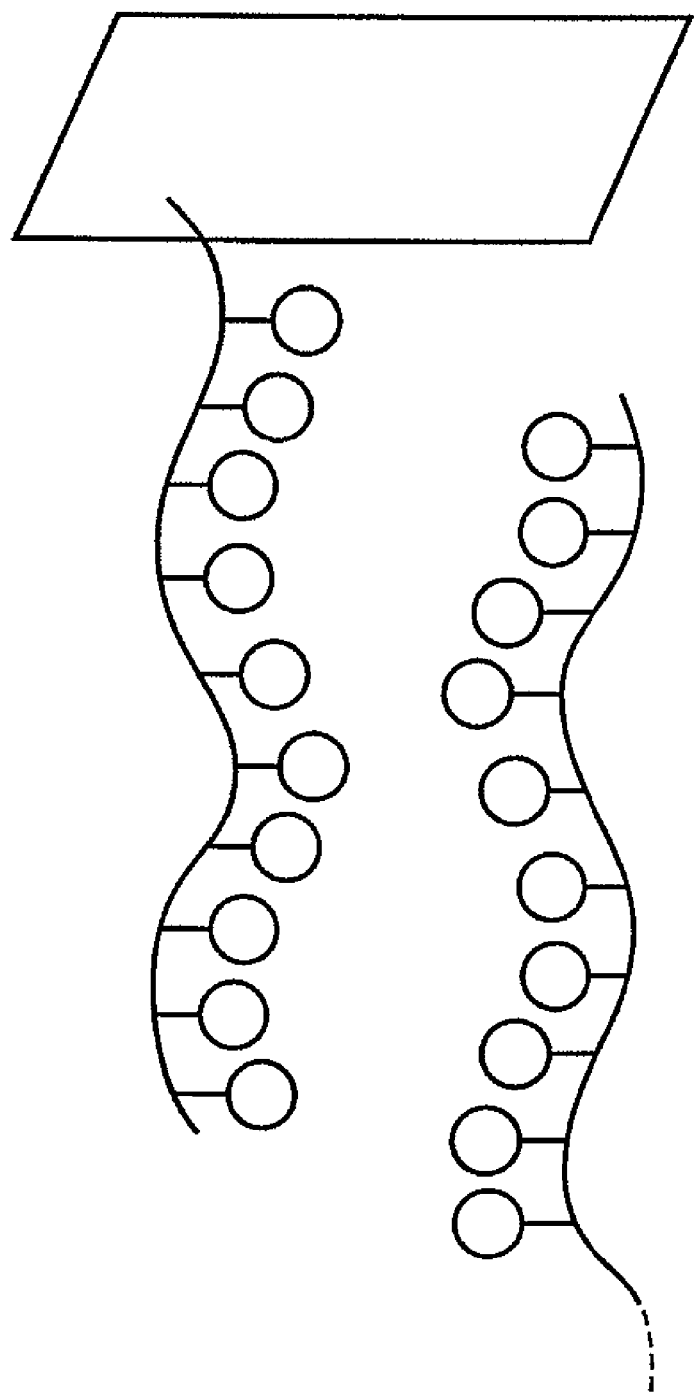
FIG. 3 is a diagram illustrating a hybridization reaction.

The nucleic acid affixed with a label is subjected to a hybridization reaction 105 with a DNA micro-array 104, which is illustrated in FIG. 3.

Preferably the probe according to the present invention is immobilized on the surface of a carrier. The probe fixed on the carrier is herein called as a probe carrier, and arranging a plurality of probes forming an array is called as a probe array.

For instance, in case of the identification of infectious pathogenic microorganisms, the DNA micro-array 104 is composed of probes specific to the microorganisms immobilized on a substrate. Thereby the probes specific to the respective microorganisms are designed with respect to genomic regions encoding e.g. 16s rRNA according to the aforementioned method. As the carrier (substrate) to fix the probes of the DNA micro-array 104, a planar substrate, such as a glass substrate, a plastic substrate and a silicon wafer, is considerable. Further, a 3D-structural body with irregularity, a spherical body, such as a bead, a rod, a string and a fiber may be used as well without influencing the aspect or the effect of the present invention.

In general, the surface of the substrate is pretreated enabling the fixation of the probe DNA. Especially the surface introduced with functional groups enabling a chemical reaction is a preferable form in terms of good reproducibility, since the probes are stably bonded during a step of a hybridization reaction. Examples of a fixation method for the present embodiment include a combination of a maleimide group and a thiol group (—SH). Namely, a thiol group (—SH) is bonded to an end of the nucleic acid probe, while the solid surface is treated to have a maleimide group, and the thiol group of the nucleic acid probe transported to the solid surface reacts with the maleimide group on the solid surface fixing the nucleic acid probe. As for a method for introducing a maleimide group, an aminosilane coupling agent is first reacted with a glass substrate, then a maleimide group is introduced by a reaction between the amino group and an EMCS reagent (N-(6-maleimidocaproyloxy) succinimide: Dojindo Lab.). A —SH group can be introduced to a DNA during synthesis of the same by a DNA automatic synthesizer using 5'-Thiol-Modifier C6 (Glen Research). Combination examples of functional groups to be used for the fixation, other than the afore-described combination of a thiol group and a maleimide group, include a combination of an epoxy group (on a solid surface) and an amino group (to the end of a nucleic acid probe). Further, a surface treatment with various silane coupling agents is also effective, and an oligonucleotide with an introduced functional group, which can react with a functional group introduced by the silane coupling agent, is used. Further, a method of coating a resin having a functional group is also applicable.

After the hybridization reaction 105, the surface of the DNA micro-array 104 is washed to remove a nucleic acid not bound to the probe, and (usually) dried. Then the intensity of the fluorescence of the hybridization reaction 105 is measured. For this purpose, the substrate of the DNA micro-array 104 is illuminated by excitation light and the fluorescence intensity is measured to obtain an image (106, 107).

The following 3 ways are possible in using a probe carrier according to the present invention:
(1) The steps 1 and 2 are carried out in the same reaction area (a reactor, a chamber), by exchanging a probe carrier for each treatment;
(2) The steps 1 and 2 are carried out in different reaction areas placing the respective probe carriers in the reaction areas, and the sample is transported between the reaction areas; and
(3) The first and second probes are arranged in a predetermined direction and fixed in a flow channel, and the sample flows in the flow channel being treated for the steps 1 and 2 in series.

A cassette having a plurality of reaction areas may be constituted favorably. A cassette is preferably so constructed as a construction disclosed in Japanese Patent Application Laid-Open No. 2007-101364 capable of hybridization and detection. It is so constructed that the first and second reaction areas and a flow channel are formed on the substrate, through which a liquid can move between the reaction areas, and transportation of the liquid and reaction take place on the substrate.

Figure 2A:
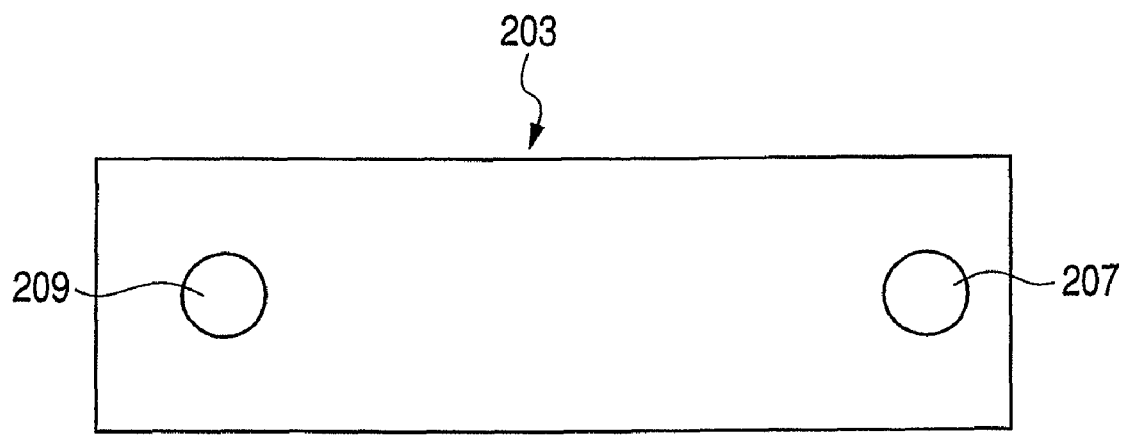
FIGS. 2A and 2B are cross-sectional views of a cassette according to an embodiment of the present invention.
Figure 2B:
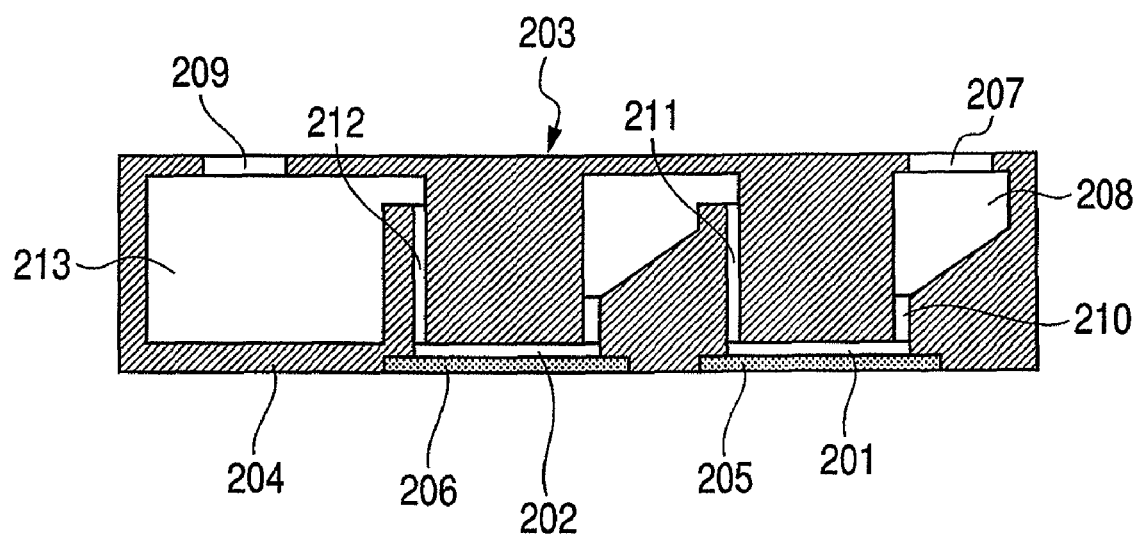

As illustrated in FIGS. 2A and 2B, a structure having a first chamber 201 as the first reaction area and a second chamber 202 as the second reaction area is preferable for successive capture treatments.

FIGS. 2A and 2B illustrate a cross-sectional view of a cassette. The cassette 203 is constituted of a housing 204, the first DNA micro-array 205 and the second DNA micro-array 206. There is an inlet 207 in the upper side of the cassette 203, through which an aliquot of a mixture liquid is filled into a liquid receiving chamber 208. At the opposite side of the inlet 207 is a suction hole 209 to suck air by contacting a suction device (not illustrated). By suction, the mixture liquid is introduced into the reaction chamber 201 through a flow channel 210, and the mixture liquid can contact the DNA micro-array 205. The temperature of the mixture liquid in the reaction chamber 201 is raised by a temperature control device (not illustrated) to promote the hybridization reaction.

Upon completion of the hybridization reaction, air is further sucked from the suction hole 209, which transports the mixture fluid through a flow channel 211 connecting the first and second chambers to the second reaction chamber 202 having the second DNA micro-array 206.

Thereby can the mixture fluid contact the second DNA micro-array 206. Next, the temperature of the mixture liquid in the reaction chamber 202 is raised by a temperature control device (not illustrated) to promote the second hybridization reaction.

Upon completion of the hybridization reaction, air is further sucked from the suction hole 209, which transports the mixture fluid through a flow channel 212 to a waist liquid chamber 213. Then, the surfaces of the first and second DNA micro-arrays 205 and 206 are washed, which is carried out by flowing a washing liquid instead of the mixture liquid.

Upon completion of the hybridization reactions, by attaching a detection system 40 (not illustrated) to the lower side of the DNA micro-arrays, the reactions between the target nucleic acids and the probe nucleic acids immobilized on the DNA micro-arrays may be identified or quantified. In case a fluorescent label is attached to the target nucleic acid, excitation light for the fluorescent label is illuminated on the DNA micro-array and fluorescence or intensities of fluorescence at the respective fixed points of the probes are measured. If the detection system is to detect fluorescence or intensity of fluorescence, the cassette 203 has a structure with a light path allowing the illumination of the excitation light and measurement of fluorescence. Using the obtained data on fluorescence the existence of the target substance or the amount in the sample is determined.

The above structure contains 2 arrays, however, a plurality of chambers with a third, fourth or further arrays may be added.

A singularity or plurality of nucleic acid probes may be used in the respective steps.

Capturing treatment in 2 separate steps give advantages over a conventional method in the following aspects.

Since the first nucleotide sequence is excluded from the calculation scope, the calculation time for designing the second probe is shortened.

Since the first nucleotide sequence is excluded from the comparison scope, a second probe, which can discriminate specifically only when the first nucleotide sequence is excluded, can be found in designing the second probe.

Since the degree of freedom in designing the second probe is enhanced, a DNA micro-array providing more probes designed with relative positions enabling more stable hybridization can be provided (see e.g. U.S. Patent Application Publication No. US-2005-0059069).

Next, a hybridization reaction, which is a basic reaction used for the capturing treatment according to the present invention, will be described.

FIG. 3 is a diagram illustrating a hybridization reaction on a DNA micro-array. Most of DNA nucleotide sequences are in the form of a double helical structure in vivo, and the double strands are bonded together by hydrogen bonds between the bases. On the other hand, RNA nucleotide sequences exist frequently as a single strand. There are 4 kinds of bases for DNA, namely A (adenine), C (cytosine), G (guanine) and T (thymine) and 4 kinds of bases for RNA, namely A, C, G and U (uracil). The hydrogen bonding is possible between the pairs of A-T(U) and G-C. Hybridization means a status where two single stranded nucleic acid molecules are bonded together through at least a part of nucleotide sequences. By a postulated scheme in the present embodiment, a nucleic acid molecule immobilized on the substrate (probe) as shown in the upper side of FIG. 3 is shorter than a nucleic acid molecule in a sample shown in the lower side. Consequently, if the nucleic acid molecule in the sample contains the nucleotide sequence of the probe, a hybridization reaction occurs capturing the target nucleic acid molecule in the sample.

Figure 4:
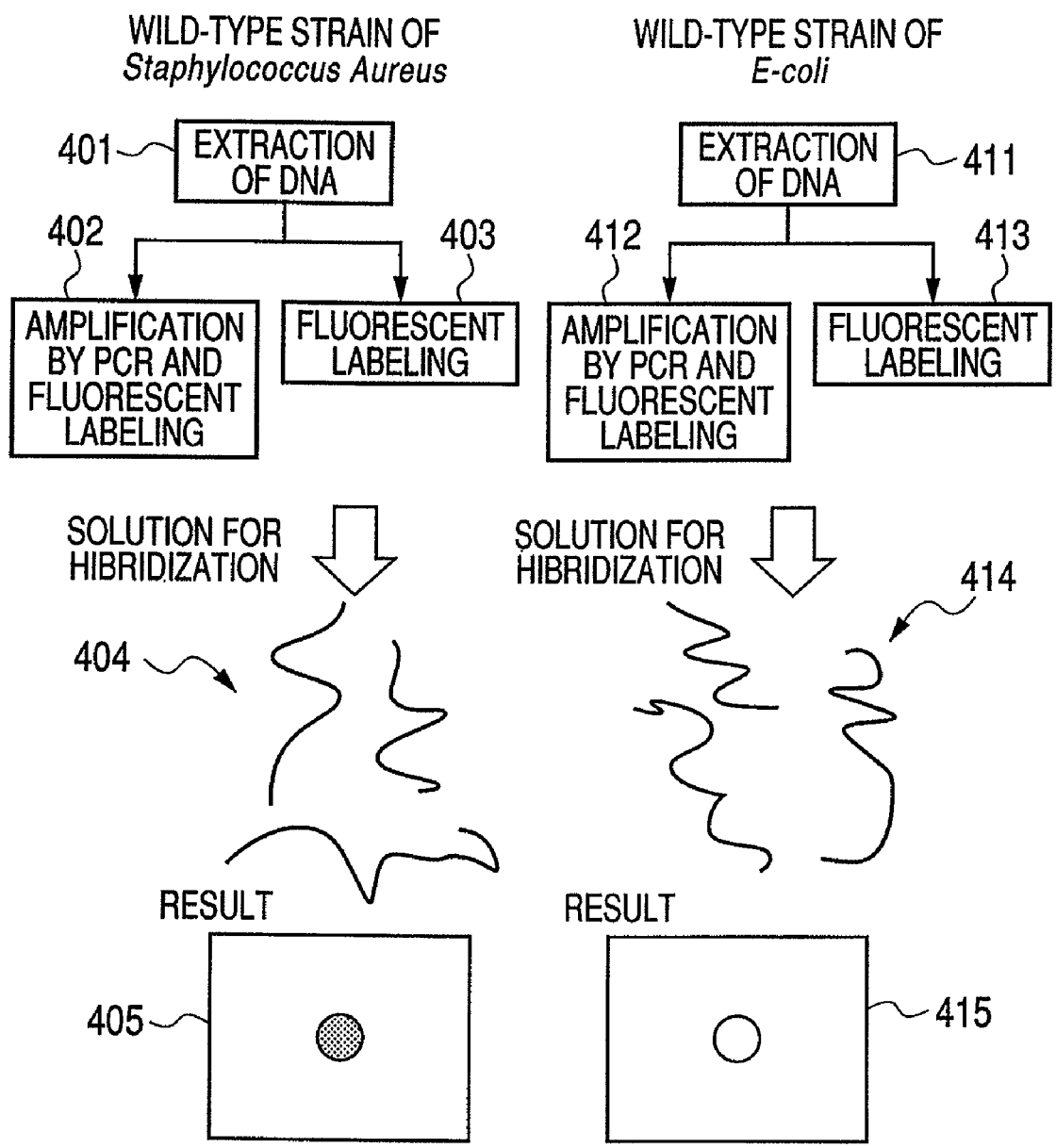
FIG. 4 is a diagram illustrating procedures in an experiment with a DNA micro-array for identification of infectious diseases.

Using FIG. 4, a principle of a DNA micro-array for identifying a microorganism causing an infectious disease will be described. It is assumed that the DNA micro-array shown in FIG. 4 is prepared for the purpose of identifying *Staphylococcus aureus*. A treatment process on the left side of FIG. 4 is for a wild-type strain of *Staphylococcus aureus*, and a treatment process on the right side is for a wild-type strain of *E. coli*. It is possible to so consider that the left is a process for treating the blood of a patient infected with *Staphylococcus aureus* and the right is a process for treating the blood of a patient infected with *E. coli*.

The treatments are basically same in both the processes. Namely, first, DNA (401, 411) is extracted from the blood or expectoration of a patient. Thereby in general human DNA originated from somatic cells of the patient may be included. In the event the extracted DNA is limited in amount, amplification by PCR, etc. is carried out. Generally at such step, a fluorescent substance or a substance which is able to bond a fluorescent substance is mixed as a label (402, 412).

If amplification is not carried out, using the extracted DNA and by forming a complementary strand a fluorescent substance or a substance which is able to bond a fluorescent substance is mixed as a label, or a fluorescent substance or a substance which is able to bond a fluorescent substance is attached directly to the extracted DNA as a label (403, 413).

For the purpose of identifying a microorganism causing an infectious disease, by PCR amplification, a part of the nucleotide sequence constituting the ribosome RNA called 16s (16s RNA) is usually amplified. In this case, substantially same PCR primers are used for *Staphylococcus aureus* (FIG. 4, left) and for *E. coli* (right). Preferably a primer set able to amplify a region coding for 16s rRNA of any microorganism is used to carry out multiplex PCR. In this case, as the result, each of the left and right solution for hybridization 404, 414 (FIG. 4) contains multiple kinds of nucleotide sequences.

If more detailed nucleotide sequence analysis is intended, a PCR primer set for *Staphylococcus aureus* and a PCR primer set for *E. coli* may be separately prepared. In this case, if primers are so designed to allow amplifying selectively certain limited parts of the genomes of the microorganisms, the kinds of nucleotide sequences included in the solutions for hybridization are extremely limited. However there are usually several microorganism strains in the nature, and it is seldom that there is only a kind of nucleotide sequence in a solution for hybridization.

If a DNA micro-array designed for identifying *Staphylococcus aureus* works correctly, the solution for hybridization 404 reacts positively with the spots 405, but the right hand side solution for hybridization 414 reacts negatively with the spots 415.

Similarly, if a DNA micro-array designed for identifying *E. coli* works correctly, the solution for hybridization 404 reacts negatively with the spots, but the solution for hybridization 414 reacts positively with the spots. Naturally, a DNA micro-array having various kinds of spots reacting specifically with the respective microorganisms may be used for identifying the infected microorganisms.

(Treatment Procedure for Detection Method)

Next, the detection method according to the present invention will be described in detail by way of an example, wherein a plurality of microorganisms are detected in turn.

Figure 5:
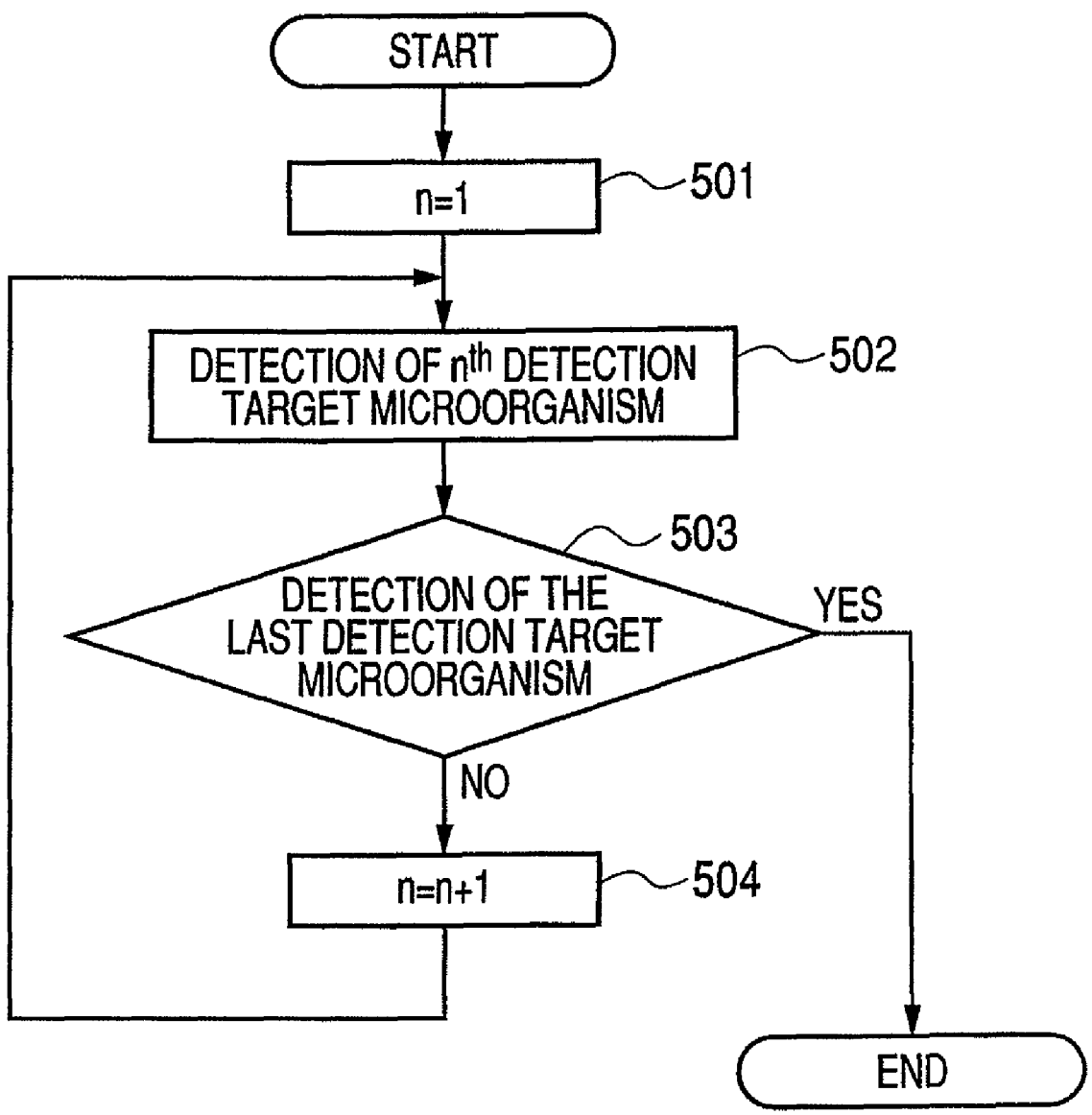
FIG. 5 is a flow-chart of a treatment procedure for detecting a plurality of microorganisms.

FIG. 5 is a flow-chart of a treatment procedure for detecting a plurality of microorganisms. Using an initially designed probe for the first microorganism, the existence of the first microorganism in a sample is detected.

Thereafter according to the order of the design, detection of the existence of a target microorganism is repeated using a detecting probe for the target microorganism as in the detection method for the existence of the first microorganism.

Figure 6:
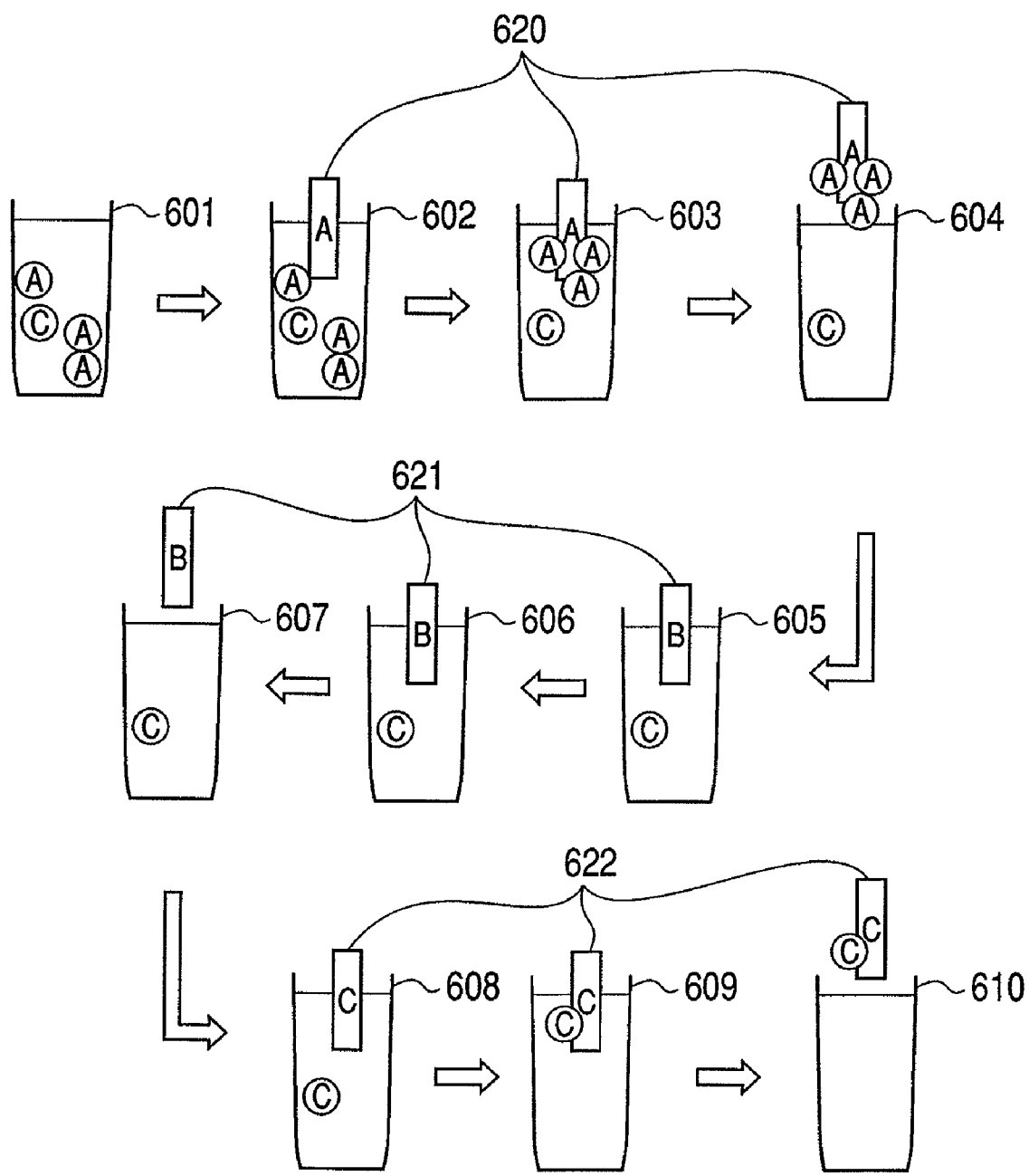
FIG. 6 is schematic diagram illustrating a summarized scheme for detecting a plurality of microorganisms.

Using FIG. 6 a scheme of the detection method for microorganisms in a sample according to the present invention will be described. Herein it is assumed that there are 3 detection target microorganisms of A, B and C, and microorganisms A and C contained in a sample, and that the probes are designed in the order of microorganisms A, B and C.

A sample is a liquid or a solid, which may potentially contain a DNA originated from the target microorganisms. The sample 601 contains A and C.

(602) The probe 620 detecting the microorganism A is hybridized with the sample.

(603) All and only the DNA originated from the microorganism A is hybridized with the abundantly existing probe 620.

(604) The existence of the microorganism A is detected by the DNA originated from the microorganism A hybridized with the probe 620. At need the hybrid product of the DNA originated from the microorganism A and the probe 620 is removed from the sample. In this case, if a probe carrier described hereinbelow, in which the probe 620 is immobilized on a solid, is used for a hybridization reaction, the removal of the DNA originated from the microorganism A from the sample after the hybridization reaction becomes easier.

(605) The probe 621 detecting the microorganism B is hybridized with the sample.

(606) All and only the DNA originated from the microorganism B is hybridized with the abundantly existing probe 621.

(607) In this example, a DNA originated from the microorganism B does not exist, and nothing hybridizes with the probe 621 to deny the existence of the microorganism B.

(608) The probe 622 detecting the microorganism C is hybridized with the sample.

(609) All and only the DNA originated from the microorganism C is hybridized with the abundantly existing probe 622.

(610) The existence of the microorganism C is detected by the DNA originated from the microorganism C hybridized with the probe 622.

A probe designed for detecting the $n^{th}$ microorganism according to the present invention may bind to a DNA originated from an $(n-1)^{th}$ or earlier microorganism. A phenomenon that a probe detects more than 1 microorganisms is called as a cross-hybridization, or non-specific bonding of a probe.

Therefore, the detection treatment of a plurality of microorganisms in a sample must be carried out in consideration of the above. It is important that detection treatment should follow the predetermined order, namely in the aforementioned embodiment, the microorganisms should be detected in the order of the probe designing.

More particularly, in step 602 the detection probe 620 for the microorganism A should preferably be abundant to hybridize the entire DNA originated from the microorganism A existing in the sample. According to the above, at the following hybridization reaction between the sample and the detection probe for the microorganism B, the detection probe for the microorganism B can avoid hybridizing with the DNA originated from the microorganism A achieving high accuracy in detecting the microorganism B in the sample, even if the same can bind nonspecifically to the DNA originated from the microorganism A.

However, all the capturing probes are not required to be detection probes, but nucleic acid not captured by the detection probes may be captured again in an additional step with large excess of capturing probes.

Similarly in step 605 the probe for the microorganism B for hybridization reaction with the sample should be used in amount large enough to hybridize the entire microorganism B that could exist in the sample to assure the accuracy of the following detection of the microorganism C.

In general, a chemical equilibrium of a hybridization reaction between a probe P and an analyte T forming a hybridization product D is expressed as below using an equilibrium constant K for hybrid formation.

$$P + T \xrightleftharpoons{K} D \qquad \text{Formula 1}$$

Putting total concentrations of P, T and the overall concentration as Cp, Ct and Call, and concentrations of P, T and D at an equilibrium as Ep, Et and Ed, Call=Cp+Ct From the law of mass action, Ed=Ep Et K From the law of the conservation of concentration, Cp=Ep+Ed Ct=Et+Ed For a probe described below, the equilibrium constant K is about $7 \times 10^{16}$.

Under the condition, where the probe concentration is high enough for the analyte to hybridize, Cp>>Ct, where Et is expected to be close to zero, and hybridization of the detection probe for the $n^{th}$ microorganism with the remaining DNA originated from the $(n-1)^{th}$ microorganism will not presumably occur.

(An Example of Designing a Set of Probes)

Embodiment 1

A designing method for designing suitable probes for the above described detection method will be described in detail. Hereinbelow, a target nucleic acid sequence is expressed as a microorganism, which may exist in a sample.

Figure 7:
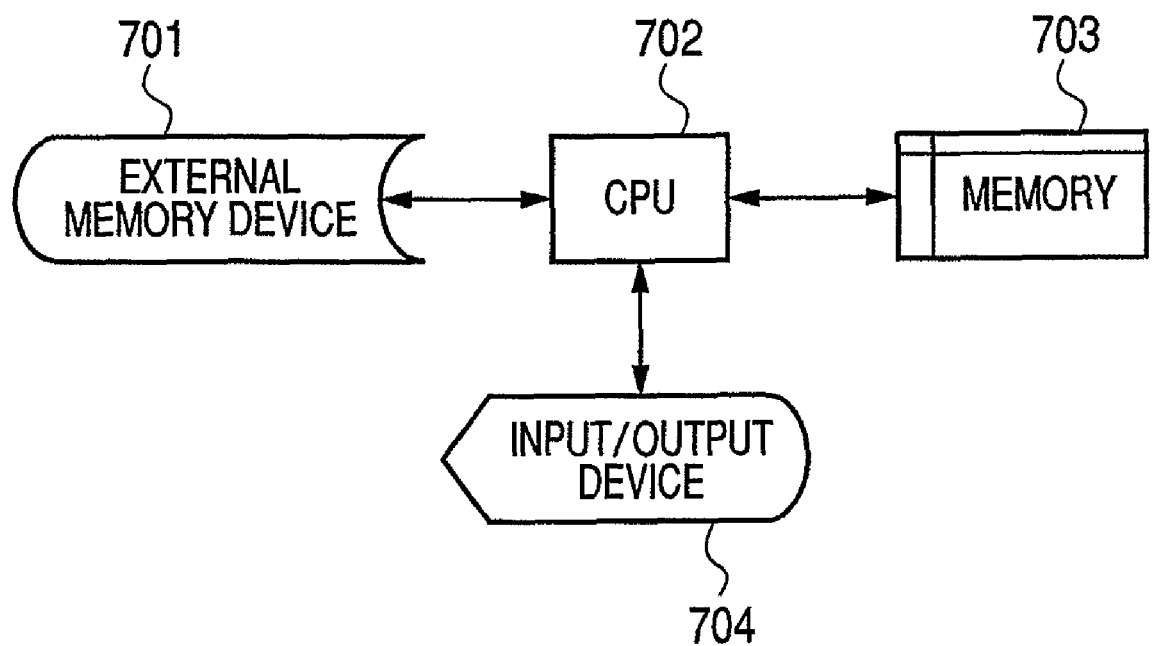
FIG. 7 is a block diagram illustrating a constitution of a data processing apparatus capable of applying the probe design method according to the present invention.

FIG. 7 is a block diagram illustrating a constitution of a data processing apparatus capable of applying the probe design method according to Embodiment 1. The designing method for probes according to the present embodiment is implemented in an apparatus constituted of an external memory device 701, CPU 702, a memory 703 and an input/output device 704. Namely, it can be implemented in a conventional personal computer, a work station, etc.

In FIG. 7 the external memory device 701 stores a program to carry out the designing method according to the present embodiment, data on various nucleotide sequences and parameters (length of DNA (oligonucleotide) probes, melting points, etc.). Further it has a function to store the probe sequences themselves selected according to the present embodiment. The CPU 702 executes the program for designing probes and controls all the devices. The memory 703 stores temporarily the program, a subroutine and data to be used by the CPU 702. The input/output device 704 includes a display, a key-board, a pointing-device, etc. for interaction with a user. Generally a trigger to execute the program to carry out the probe designing method according to the present embodiment is pulled by a user by means of the input/output device. Further, review of the results or regulation of parameters of the program by a user is carried out by means of the input/output device.

Figure 8:
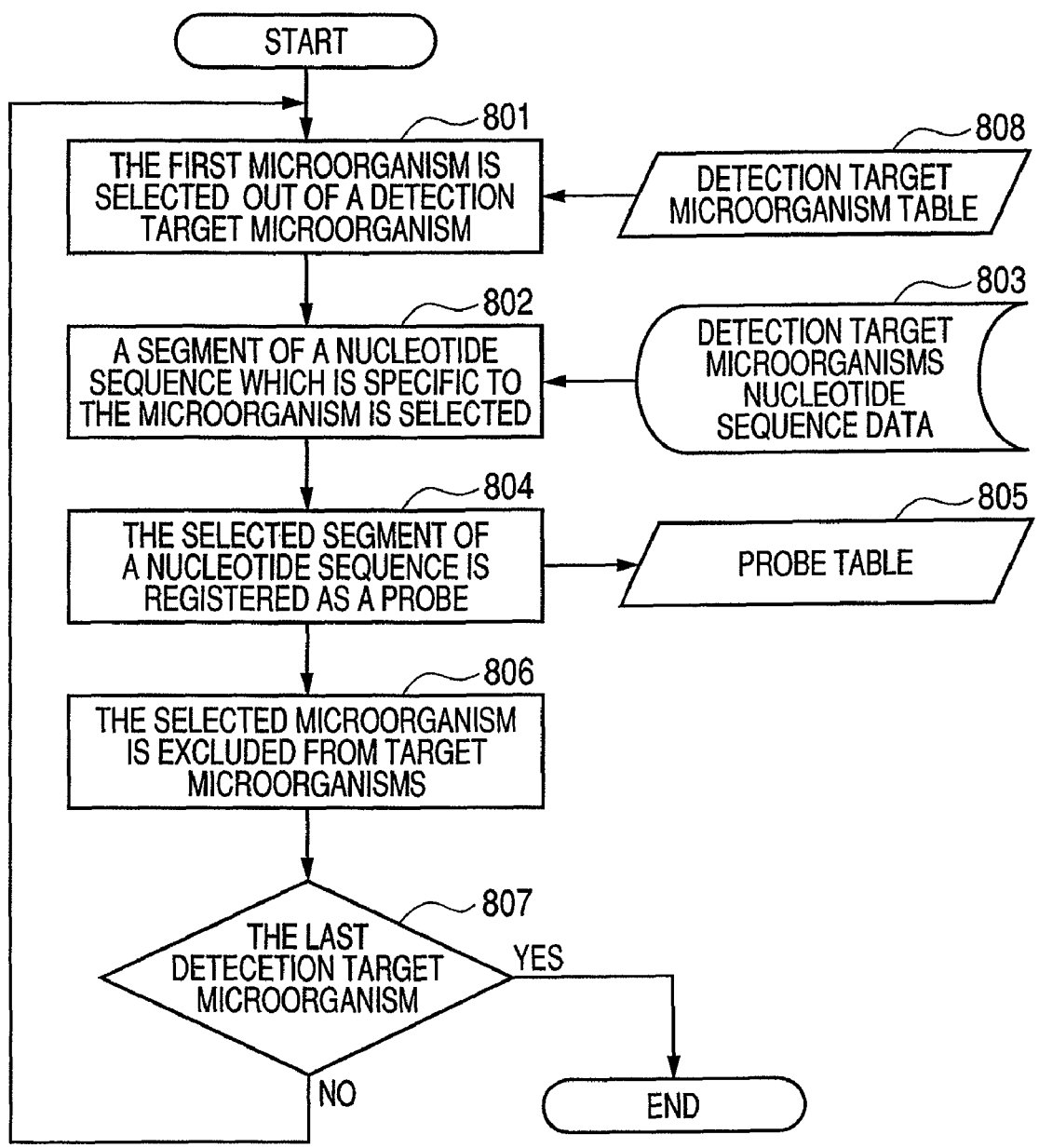
FIG. 8 is a flow-chart illustrating the probe design method according to the present invention.

FIG. 8 is a flow-chart illustrating the probe design method according to Embodiment 1. In the first step 801, the first microorganism is selected out of a detection target microorganism table 808 as the first sequence.

In the target microorganism table, nucleotide sequences of a plurality of detection target microorganisms are stored as target nucleotide sequences. The nucleotide sequence data are read out in the process of probe designing at need. When a nucleotide sequence to be used as a probe according to the present invention for a microorganism is decided, it will be registered in a probe table.

In such case, the microorganism with the highest specificity may be chosen as the first microorganism. Focusing on a partial nucleotide sequence of a detection target microorganism, and if the same is not identical to any partial nucleotide sequences of other detection target microorganisms, such partial nucleotide sequence is called herein as having "specificity". A microorganism having many such specific partial nucleotide sequences, or a specific and relatively long base-length partial nucleotide sequence may be called as "a microorganism with high specificity".

For instance, to detect a 1500-base-long DNA of *Staphylococcus aureus*, a probe corresponding to *Staphylococcus aureus* must be prepared. If a probe of 50 bases should be prepared, there are 1451 kinds of partial nucleotide sequences as probe candidates. The above can be analogized easily from the consideration that there is 1 candidate for a 1500-base-long probe, 2 for a 1499-base-long probe and 1500 for a 1-base-long probe.

In the second step 802, the nucleotide sequence of the first microorganism is read out from the detection target microorganisms nucleotide sequence data 803, and a nucleotide sequence which is a segment of the read-out nucleotide sequence and specific to the first microorganism, and is not identical to any segments other than nucleotide sequences of the gene of the first microorganism, is selected.

The detection target microorganisms nucleotide sequence data are registry of nucleotide sequences corresponding to e.g. *Staphylococcus aureus* or *Pseudomonas aeruginosa*. All the partial nucleic acid sequences included in the M-base-long first microorganism can be candidates for a probe. Consequently there are total 1+2+3+ . . . +M=M (M+1)/2 kinds of nucleotide sequences to be used as a probe. Herein, all the partial nucleotide sequences included in a detection target microorganism are called as probe candidates.

Next, if there are n-kinds of detection target microorganisms, the afore-obtained probe candidates of the first microorganism are examined, if there is a congruent sequence in partial nucleotide sequences of any of (n-1)-kinds of the detection target microorganisms excluding the first microorganism itself. Thus the first nucleotide sequence for the first microorganism is determined.

The examining step is exercised by the afore-described data processing apparatus. There are many examination methods and further detail is not herein described. If, for example, a partial nucleotide sequence of ATTGAT contained in the first microorganism should not be included in any of partial sequences of other (n-1)-kinds, the nucleotide sequence of ATTGAT is deemed as a specific sequence characterizing the first microorganism.

In step 804, the determined first nucleotide sequence is output for registration as a detection probe for the first microorganism on the probe table 805. Thus the nucleotide sequence of the probe for the first microorganism is determined. There are no particular restrictions on the number of kinds of the microorganisms, if the microorganism are to be selected previously, for which probes be prepared, the probe designing method according to the present invention can be applied to any of n-kinds of microorganisms (n is 2 or higher) selected at discretion.

In the third step 806, the first microorganism is excluded from target microorganisms of the next and later procedures. This is done because the first microorganism is specific to any other target microorganisms.

In step 807 by checking if there remain 2 or more detection target microorganisms to be determined for the probe, if yes, then in step 801 as described above the first sequence is excluded from the target sequences, and the second microorganism (the second sequence) is selected from the new excluded target sequences.

As in the second step, from partial sequences included in the second sequence the second nucleotide sequence not identical to any part of partial sequences of the target nucleotide sequences excluding the second sequence is determined and such second partial sequence is determined for the second probe.

Then as in the third step, the second microorganism (the second sequence) is excluded from treatment target microorganisms of the next and later procedures.

The steps are repeated in turn to determine the respective probes for the first to the $n^{th}$ microorganism one-by one (n is an integer of 2 or higher). Namely, for the $n^{th}$ sequence the $n^{th}$ partial sequence is determined as the $n^{th}$ sequence probe. In this regard, it is important to note that the $n^{th}$ probe for microorganism is not necessarily designed specific to the $(n-1)^{th}$ microorganism. This is effective in shortening the time required for designing probes, even if the number of the detection target microorganisms is increased. There are no particular restrictions on the selection order of the n-kinds of microorganisms, and at probe designing, selection in the descending order of detection rates (a detection rate is a ratio of the number of patients infected with a target microorganism to the total number of patients of infectious diseases), or in the descending order of seriousness of symptoms caused by a microorganism may be adopted.

When in step 807 nucleotide sequences to be used by probes for the entire detection target microorganisms are determined, the procedure is finished.

If a specific nucleotide sequence cannot be found in the first selected microorganism, another sequence may be selected newly as the first microorganism. This may increase a chance of finding a specific sequence for the microorganism, which has failed once in finding a specific sequence, owing to decrease in the target microorganisms.

Embodiment 2

In the above Embodiment 1 a method for designing a probe for each selected target microorganism at a step is described.

Hereinbelow an embodiment will be described, wherein at a selection step a probe group consisting of a plurality of probes is selected for designing the respective probes.

Although in Embodiment 1 in the first step 801 the one first microorganism is selected out of the detection target microorganism table 808, herein as the first microorganism group several kinds of microorganisms are selected instead of the first microorganism.

In the second step 802 the nucleotide sequences of the first microorganism group are read out from the detection target microorganism nucleotide sequence data 803, and out of the read-out nucleotide sequences such nucleotide sequences, as binding to specific segments of the first microorganism group, but not identical to any part of the nucleotide sequences of the genes of the first group, are determined.

It is important to note that the nucleotide sequences of other microorganisms in the first microorganism group are also the subjects of the examination.

Then the microorganisms in the first group are excluded from the target microorganisms for the next and later procedures, as in Embodiment 1.

In step 807 is checked if there remain 2 or more detection target microorganism groups to be determined for the probe, if yes, then from step 801 the first step, the second step and the third step are repeated step-by-step.

According to the above, probes for the first microorganism group to the $n^{th}$ microorganism group respectively are determined successively (n is an integer of 2 or higher).

Since probes are determined for the respective microorganism groups according to the present Embodiment, a plurality of micro-arrays attached with the probes are prepared and used suitably in a form as shown in FIGS. 2A and 2B, with which a sample is subjected to capture treatments in series.

Other Embodiments

Needless to say, an object of the present invention is achieved also by providing a probe designing system or apparatus with a storage medium storing program coding for a software realizing the function of the afore-described probe designing method, so that a computer (or CPU or MPU) of the system or apparatus reads out the program coding stored in the storage medium and executes the same.

In such a case, the program coding per se read out of the storage medium realizes the function of the afore-described embodiments, and therefore the storage medium storing the program coding constitutes the present invention.

As the storage medium providing the program coding, a flexible disk, a hard disk, an optical disk, a magneto-optical disk, CD-ROM, CD-R, a magnetic tape, a nonvolatile memory card, ROM, etc. can be used.

Naturally, in addition to the realization of the function of the afore-described embodiments by executing the program coding read out by the computer, a part or all of the jobs may be executed by the OS etc. running on the computer according to a command of the program coding realizing the function of the afore-described embodiments.

Needless say another mode is possible, wherein the program coding read out of the storage medium is stored in a memory of an expansion board inserted to a computer or an expansion unit connected with a computer, and a CPU of the expansion board or the expansion unit executes a part or all of the practical jobs according to a command of the program coding realizing the function of the afore-described embodiments.

Concrete experiment procedures of a DNA micro-array suitable for realizing the present invention will be now described.

(1. Preparation of a Probe DNA)

A nucleic acid sequence is designed according to Embodiment 1 for a probe detecting *Enterobacter cloacae*. More particularly, designing is carried out by a method described in Embodiment 1 based on a genomic region coding for 16s rRNA. Regarding a database, the NCBI database is utilized. The following 10 microorganisms are selected as the targets of the detection, which may exist in a sample.
(1) *Enterobacter cloacae*
(2) *Staphylococcus aureus*
(3) *Staphylococcus epidermidis*
(4) *E. coli*
(5) *Klebsiella pneumoniae*
(6) *Pseudomonas aeruginosa*
(7) *Serratia* bacteria
(8) *Streptococcus pneumonia*
(9) *Hemophilus influenzae*
(10) *Enterococcus faecalis*

Next, excluding the nucleotide sequence of (1) *Enterobacter cloacae* from the target sequence, and out of the nucleotide sequences of the 9 microorganisms from (2) to (10), a sequence specific to the nucleotide sequence of (2) *Staphylococcus aureus* is extracted to design a probe for *Staphylococcus aureus*.

Similarly, excluding the nucleotide sequence of (2) *Staphylococcus aureus* from the target sequence, out of the nucleotide sequences of the 8 microorganisms from (3) to (10), a sequence specific to the nucleotide sequence of (3) *Staphylococcus epidermidis* is extracted to design a probe for *Staphylococcus epidermidis*.

A microorganism, for which a specific sequence is extracted, is excluded and the extraction treatment of a specific sequence concerning a certain microorganism out of the remaining nucleotide sequences is repeated for the microorganisms (1) to (10) in turn, all probes for the microorganisms (1) to (10) can be designed.

In order to fix the probes on a DNA array, after the synthesis a thiol group is introduced as a functional group to the 5' end of the nucleic acid according to a commonly used method. After the introduction of the functional group, the probe is purified and freeze-dried. The freeze-dried probes are stored in a freezer at −30° C.

(2. Preparation of Primers for PCR Amplification of a Sample)

Nucleic acid sequences of PCR primers are designed for amplification of 16s rRNA nucleic acid (a target nucleic acid) for detecting a pathogenic microorganism.

More particularly, a primer set amplifying specifically a genomic region encoding 16s rRNA, namely primers having specific melting temperatures as uniform as possible at the both ends of the approximately 1500-base-long 16s rRNA coding region are designed. Preferably, to enable simultaneous amplification of mutants or a plurality of 16s rRNA coding regions existing on the genome, a plurality of primers should be designed.

After the synthesis the primers are purified by high performance liquid chromatography (HPLC), and 3 kinds of forward primers and 3 kinds of reverse primers are mixed and dissolved in a TE buffer solution to the final concentrations of the respective primers of 10 pmol/μL.

(3. Extraction of *Enterobacter cloacae* Genome DNA (A Model Sample))

(3.1 Microbial Culture and Pretreatment for Genome DNA Extraction)

A type strain of *Enterobacter cloacae* is cultured by a commonly used method. Into a 1.5 mL-capacity microtube 1.0 mL of the microbial culture fluid (OD600=0.7) is collected and subjected to centrifugation (8500 rpm, 5 min, 4° C.) to recover microbial cells. After discarding the supernatant, 300 μL of an enzyme buffer (50 mM Tris-HCl: pH 8.0, 25 mM EDTA) is added and reslurried with a mixer. The reslurried microbial suspension is subjected to centrifugation again to recover microbial cells (8500 rpm, 5 min, 4° C.). After discarding the supernatant, the following enzyme solutions are added to the recovered microbial cells and reslurried with a mixer.

Lysozyme 50 μL (20 mg/mL in an Enzyme Buffer)
N-acetylmuramidase SG 50 μL (0.2 mg/mL in an Enzyme Buffer)

Next, the microbial suspension reslurried by addition of the enzyme solutions is kept in an incubator at 37° C. for 30 min to lyse cell walls.

(3.2 Extraction of Genome)

Extraction of a microbial genome DNA is carried out using a kit for nucleic acid purification (MagExtractor-Genome-, Toyobo).

More particularly, into the pretreated microbial suspension 750 μL of a dissolving adsorbing liquid and 40 μL of magnetic beads are added and the suspension is mixed vigorously using a tube mixer for 10 min (first step).

Next, a micro-tube is placed on a separation stand (Magical Trapper) and left standing for 30 seconds to collect the magnetic beads on the wall surface. Then staying on the stand, the supernatant is discarded (second step).

After adding 900 μL of a washing liquid and mixing for 5 sec by a mixer, a reslurried suspension is prepared (step 3).

Next, a micro-tube is placed on a separation stand (Magical Trapper) and left standing for 30 seconds to collect the magnetic beads on the tube wall surface. Then staying on the stand, the supernatant is discarded (step 4).

By repeating the steps 3 and 4 the second washing is carried out (step 5), then 900 μL of 70% ethanol is added and mixed for 5 sec by a mixer, and a reslurried suspension is prepared (step 6).

Next, a micro-tube is placed on a separation stand (Magical Trapper) and left standing for 30 seconds to collect the magnetic beads on the tube wall surface. Then staying on the stand, the supernatant is discarded (step 7).

After the second washing with 70% ethanol is carried out by repeating the steps 6 and 7 (step 8), to the recovered magnetic beads 100 μL of pure water is added, which is then subjected to agitation by a tube mixer for 10 min.

Next, a micro-tube is placed on a separation stand (Magical Trapper) and left standing for 30 seconds to collect the magnetic beads on the tube wall surface. Then staying on the stand, the supernatant is recovered in a new tube.

(3.3 Examination of the Recovered Genome DNA)

The recovered microbial (*Enterobacter cloacae*) genome DNA is subjected to agarose gel electrophoresis and absorbance measurement at 260/280 nm as commonly carried out, to examine the quality (contamination of short nucleic acids, degree of degradation) and the harvested amount.

According to the afore-described treatment, about 10 μg of genome DNA was harvested, which was free from degraded genome DNA or contaminant rRNA. The harvested genome DNA is dissolved in a TE buffer solution to the final concentration of 50 ng/μL to be used in the following experiment procedures.

(4. Preparation of DNA Micro-arrays)

(4.1 Washing of a Glass Substrate)

A synthetic quartz glass substrate (size: 25 mm×75 mm×1 mm, Iiyama Precision Glass Co.) is placed in a heat and alkali resistant rack and dipped in a cleaning fluid adjusted to a predetermined concentration for ultrasonic washing. After dipping overnight in the cleaning fluid, sonication is carried out for 20 min. After taking out and washing lightly with pure water the substrate, sonication is carried out for another 20 min in ultrapure water. Then the substrate is immersed for 10 min in a 1 N aqueous solution of sodium hydroxide heated to 80° C. Then after washing again with pure water and ultrapure water, a quartz substrate for a DNA chip is ready.

(4.2 Surface Treatment)

A silane coupling agent KBM-603 (Shin-Etsu Chemical Co.) is dissolved in pure water to the concentration of 1% and agitated at room temperature for 2 hours. The previously washed glass substrate is immersed in the silane coupling agent aqueous solution and left at room temperature for 20 min. After lifting the glass substrate, washing lightly the surface with pure water, and blowing nitrogen on the both sides of the glass substrate to dry it. The dried substrate is baked for 1 hour in an oven heated to 120° C. to complete the silane coupling agent treatment, and then amino groups are introduced on the substrate surface. Next, N-(6-maleimidocaproyloxy) succinimide (herein after abbreviated as "EMCS", Dojindo Lab.) is dissolved in a 1:1 mixed solvent of dimethyl sulfoxide and ethanol to prepare a EMCS solution of the final concentration of 0.3 mg/mL. The baked glass substrate is, after cooling down, dipped in the prepared EMCS solution at room temperature for 2 hours. By the above treatment, the amino groups introduced on the surface by means of the silane coupling agent and succinimide groups of EMCS react to introduce maleimide groups on the surface of the glass substrate. The glass substrate pulled out of the EMCS solution is washed with the mixed solvent as used for dissolving EMCS, then washed with ethanol and dried under nitrogen atmosphere.

(4.3 Probe DNA)

The detection probe for a microbe prepared in the procedure 1 is dissolved in pure water and aliquoted to the amount corresponding to the final concentration of 10 µM when filled in the ink tank and then freeze-dried to remove water.

(4.4 Extrusion of DNA by a Bubble Jet Printer and Bonding to the Substrate)

An aqueous solution containing glycerin 7.5 wt %, thiodiglycol 7.5 wt %, urea 7.5 wt % and Acetynol EH (Kawaken Fine Chemical Co.) 1.0 wt % is prepared. The previously prepared 7 probes (Table 1) are respectively dissolved in the aforementioned mixed solvent to the predetermined concentration. The obtained DNA solutions are filled in an ink tank of a Bubble Jet® printer (BJF-850, Canon Inc.), which is mounted on a printing head.

The used Bubble Jet® printer is so modified that it can print a plate. The Bubble Jet® printer can spot about 5 pL of a DNA solution at about 120 µm pitch, by inputting a printing pattern according to a defined filing protocol.

Next, an array is prepared by printing a glass substrate with the modified Bubble Jet® printer. After confirming that printing is conducted correctly, the glass substrate is placed in a humidifying chamber for 30 min to cause a reaction between a maleimide group on the surface of the glass substrate and a thiol group at the end of a nucleic acid probe.

In this example, 10 glass slides are used to prepare one each array for each microorganism.

(4.5 Washing)

After a reaction for 30 min, the remaining DNA solution on the surface is washed away with a 10 mM phosphate buffer solution (pH 7.0) containing 100 mM NaCl, to obtain a DNA micro-array with a single strand DNA immobilized on the surface of the glass substrate.

(5. Amplification of a Sample and Labeling (PCR Amplification and Introduction of a Fluorescence Label))

Amplification of microbial DNA as a sample, and a labeling reaction are described below.

TABLE 2

| Premix PCR Reagent (TAKARA ExTaq) | 25 µl | |
|---|---|---|
| Template Genome DNA | 2 µl | (100 ng) |
| Forward Primer mix | 2 µl | (20 pmol/tube each) |
| Reverse Primer mix | 2 µl | (20 pmol/tube each) |
| Cy-3 dUTP (1 mM) | 2 µl | (2 nmol/tube) |
| H$_2$0 | 17 µl | |
| Total | 50 µl | |

The reaction solution of the above composition is amplified according to the following protocol using a commercially available thermal cycler.

TABLE 3

| 95° C. | 10 min. | |
|---|---|---|
| 92° C. | 45 sec. | |
| 55° C. | 45 sec. | 35 Cycles |
| 72° C. | 45 sec. | |
| 72° C. | 10 min. | |

After the amplification reaction, the primers are removed by a purification column (QIAquick PCR purification kit, QIAGEN) and the amplified product is quantified and used as a labeled sample.

(6. Hybridization)

A detection reaction is conducted using a DNA micro-array prepared in (4. Preparation of DNA micro-arrays) and a labeled sample prepared in (5. Amplification of a sample and labeling (PCR amplification and introduction of a fluorescence label)).

(6.1 Blocking of a DNA Micro-array)

BSA (Albumin from bovine serum Fraction V, Sigma-Aldrich) is dissolved in a 100 mM NaCl/10 mM phosphate buffer solution to the 1 wt % concentration. The DNA micro-array prepared in (Preparation of DNA micro-arrays) is immersed for blocking in the solution at room temperature for 2 hours. After the blocking treatment the array is washed with a 2×SSC solution (300 mM NaCl/30 mM sodium citrate (trisodium citrate dihydrate, $C_6H_5Na_3.2H_2O$), pH 7.0) containing 0.1 wt % of SDS (sodium dodecyl sulfate), then rinsed with pure water and dehydrated by a spin drier.

(6.2 Hybridization)

The dehydrated DNA micro-array is placed on a hybridization station (Genomic Solutions Inc.) for a hybridization reaction with the hybridization solution and under the conditions as described below.

Hybridization Solution

6×SSPE/10% formamide/Sample (the whole products of the second PCR), (thereby 6×SSPE: 900 mM NaCl/60 mM NaH$_2$PO$_4$.H$_2$O/6 mM EDTA, pH7.4)

Hybridization Conditions

Reacted at 65° C. for 3 min, then at 92° C. for 2 min, then at 45° C. for 3 hours, then washed with a solution of 2×SSC/0.1% SDS at 25° C., then washed again with 2×SSC at 20° C., then rinsed with pure water manually, and then spin-dried.

(7. Detection of Microbe (Fluorescence Measurement))

The fluorescence measurement of the DNA micro-array after the hybridization reaction is conducted with a DNA micro-array scanner for fluorescence detection (GenePix 4000B, Axon Instruments).

As described above, designing of an oligonucleotide probe optimal to a DNA micro-array system can be realized according to the present embodiment, which can work further for obtaining accurate identification information on biological species and individuals.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2007-103853, filed Apr. 11, 2007, which is hereby incorporated by reference herein in its entirety.

What is claimed is:

1. A method for detecting a nucleic acid in a liquid sample, comprising:
   a first capturing step, in which a singularity or a plurality of first probes immobilized on a surface of a carrier and capable of specifically capturing a particular first nucleotide sequence out of a plurality of nucleic acid sequences potentially present in the liquid sample are prepared and the first probes capture the first nucleotide sequence in the liquid sample such that the first nucleotide sequence is practically excluded from the liquid sample;
   a separating step, in which the liquid sample is separated from the carrier on which the singularity or plurality of first probes are immobilized;
   a second capturing step, in which a singularity or a plurality of second probes immobilized on a surface of a carrier and capable of specifically capturing a particular second nucleotide sequence out of the plurality of nucleic acid sequences excluding the first nucleotide sequence captured by the first probes are prepared and the second probes capture the second nucleotide sequence in the liquid sample having passed through the first capturing step, wherein the liquid sample is not in contact with the carrier on which the singularity or plurality of first probes are immobilized when the second probes capture the second nucleotide sequence; and
   detecting the presence or amount of at least one of the first nucleotide sequence captured in the first capturing step and the second nucleotide sequence captured in the second capturing step,
   wherein the second probes comprise a probe which can discriminate specifically only when the first nucleotide sequence is practically excluded from the liquid sample.

2. The method according to claim 1, wherein the first capturing step and the second capturing step are carried out in an identical reaction region.

3. The method according to claim 1, wherein the first capturing step is carried out in a first reaction region and the second capturing step is carried out by moving the liquid sample to a second reaction region after the first capturing step.

4. The method according to claim 3, wherein the first reaction region, the second reaction region and a flow channel, through which a fluid can be transported between the reaction regions, are formed on a substrate, on which the transport of the fluid and reactions are carried out.

5. A method according to claim 1, wherein the singularity or plurality of first probes are used in excess of the amount of the first nucleotide sequence in the liquid sample.

6. A method for detecting a nucleic acid in a liquid sample, comprising:
   a first capturing step for capturing a first group of target nucleic acids from the liquid sample using a first carrier having a surface on which a plurality of first probes are immobilized,
   a separating step, in which the liquid sample is separated from the first carrier;
   a second capturing step after the separating step for capturing a second group of target nucleic acids from the liquid sample using a second carrier having a surface on which a plurality of second probes are immobilized,
   detecting the presence or amount of at least one of the target nucleic acids captured in the first capturing step and the second capturing step,
   wherein the first probes are capable of specifically capturing the first group of target nucleic acids,
   wherein the second probes are capable of specifically capturing the second group of target nucleic acids when the first group of target nucleic acids are practically excluded from the liquid sample, and
   wherein the second probes comprise a probe which can discriminate specifically only when the first group of target nucleic acids are practically excluded from the liquid sample.

7. The method according to claim 6, further comprising
   a third capturing step after the separating step for capturing a third group of target nucleic acids from the liquid sample using a third carrier having a surface on which a plurality of third probes are immobilized,
   wherein the third probes are capable of specifically capturing a third group of target nucleic acids when the first group of target nucleic acids and the second group of target nucleic acids are excluded from the liquid sample.

8. A method for detecting a nucleic acid in a liquid sample, comprising:
   a first capturing step, in which a singularity or a plurality of first probes immobilized on a surface of a carrier and capable of specifically capturing a particular first nucleotide sequence out of a plurality of nucleic acid sequences potentially present in the liquid sample are prepared and the first probes capture the first nucleotide sequence in the liquid sample such that the first nucleotide sequence is practically excluded from the liquid sample;
   a separating step, in which the liquid sample is separated from the carrier on which the singularity or plurality of first probes are immobilized;
   a second capturing step, in which a singularity or a plurality of second probes immobilized on a surface of a carrier and capable of specifically capturing a particular second nucleotide sequence out of the plurality of nucleic acid sequences excluding the first nucleotide sequence captured by the first probes are prepared and the second probes capture the second nucleotide sequence in the liquid sample having passed through the first capturing step, wherein the liquid sample is not in contact with the carrier on which the singularity or plurality of first probes are immobilized when the second probes capture the second nucleotide sequence; and
   detecting the presence or amount of at least one of the first nucleotide sequence captured in the first capturing step and the second nucleotide sequence captured in the second capturing step,
   wherein the second probes are capable of binding to the first and second nucleotide sequences, and the first nucleotide sequence is practically excluded from the liquid sample by the first capturing step so that the second probes bind to the second nucleotide sequence.

9. A method for detecting a nucleic acid in a liquid sample, comprising:
   a first capturing step for capturing a first group of target nucleic acids from the liquid sample using a first carrier having a surface on which a plurality of first probes are immobilized, a separating step, in which the liquid sample is separated from the first carrier;

a second capturing step after the separating step for capturing a second group of target nucleic acids from the liquid sample using a second carrier having a surface on which a plurality of second probes are immobilized, detecting the presence or amount of at least one of the target nucleic acids captured in the first capturing step and the second capturing step, wherein the first probes are capable of specifically capturing the first group of target nucleic acids, wherein the second probes are capable of specifically capturing the second group of target nucleic acids when the first group of target nucleic acids are practically excluded from the liquid sample, and wherein the second probes are capable of binding to the first and second groups of target nucleic acids, and the first group of target nucleic acids are practically excluded from the liquid sample by the first capturing step so that the second probes bind to the second group of target nucleic acids.

* * * * *